United States Patent
Fang et al.

[11] Patent Number: 6,161,421
[45] Date of Patent: *Dec. 19, 2000

[54] INTEGRATED ETHANOL GAS SENSOR AND FABRICATION METHOD THEREOF

[75] Inventors: Yean-Kuen Fang, Tainan; Jyhyi Ho, Kaohsiung Hsien; C. H. Chen, Miaoli, all of Taiwan

[73] Assignee: National Science Council, Taiwan

[*] Notice: This patent issued on a continued prosecution application filed under 37 CFR 1.53(d), and is subject to the twenty year patent term provisions of 35 U.S.C. 154(a)(2).

[21] Appl. No.: 08/987,813

[22] Filed: Dec. 10, 1997

[30] Foreign Application Priority Data

Oct. 27, 1997 [TW] Taiwan .................................. 86115896

[51] Int. Cl.[7] .......................... G01N 27/00; G01N 27/06; H01L 29/66
[52] U.S. Cl. ...................... 73/31.05; 73/23.31; 73/31.06; 422/90; 422/94; 338/34
[58] Field of Search ................................ 73/31.05, 31.06, 73/23.31, 23.2; 338/34; 422/90, 98, 94, 68.1

[56] References Cited

U.S. PATENT DOCUMENTS

| | | | |
|---|---|---|---|
| 4,343,768 | 8/1982 | Kimura | 422/97 |
| 4,580,439 | 4/1986 | Manaka | 73/23.31 |
| 4,703,555 | 11/1987 | Hubner | 338/34 |
| 4,885,929 | 12/1989 | Kasahara et al. | 73/23.31 |
| 5,019,885 | 5/1991 | Yagawara et al. | 338/34 |
| 5,698,771 | 12/1997 | Shields et al. | 73/31.05 |
| 5,767,388 | 6/1998 | Fleischer et al. | 73/31.06 |

*Primary Examiner*—Hezron Williams
*Assistant Examiner*—J. David Wiggins
*Attorney, Agent, or Firm*—Randall J. Knuth

[57] ABSTRACT

The present invention discloses an integrated ethanol gas sensor and fabrication thereof. The present invention utilities micro electro mechanical system (MEMS) technology and has a main sensing part in the form of a cantilever-bridge structure made of SiC thin film material arranged over a silicon substrate. The present invention integrates an SiC heater of comb or finger electrode shape and an $SnO_2$ thin film gas sensing element applied over distinct portions on the same Si substrate together with Al2O3 and SnO2 thin films via a VLSI technology.

8 Claims, 9 Drawing Sheets

INTEGRATED ETHANOL GAS SENSOR AND FABRICATION METHOD THEREOF

BACKGROUND OF THE INVENTION

1. Field of the Invention

The present invention relates to an integrated ethanol gas sensor and fabrication method thereof, and especially relates to an integrated ethanol gas sensor and fabrication method thereof, which applies micro electro-mechanical system (MEMS) technology to use a cantilever-bridge structure as a main sensor element structure, and integrates SiC heater with $SnO_2$ thin film on the same silicon substrate via VLSI technology.

2. Description of the Related Art

There are currently three kinds of current gas sensors, based on fabrication methods: sintering gas sensors, thick film gas sensors and thin film gas sensors. The working principles of the thin film gas sensors are stated as follows.

First, a metal oxide thin film, such as $SnO_2$, $ZnO_2$, $Fe_2O_3$. . . etc is deposited on a silicon substrate. When a test gas is absorbed by the metal oxide thin film, the conductivity of a sensing element is changed and the concentration of the test gas is identified.

In the case of $SnO_2$ thin film, two main reaction modes which occur during the test, are stated as follows.

(1) Forming a Schottky contact on the thin film:

When a molecule of the test gas approaches the thin film, if the electrophilic of the test gas is higher than the power function of the semiconductor material, the test gas molecule scratches a conduction electron from the conduction band of the semiconductor material. Therefore, the conductivity of the semiconductor material is reduced. In contrast, if the electrophilic of the test gas is lower than the power function of the semiconductor material, the conductivity of the semiconductor is raised.

(2) Reaction between the test gas and the gas absorbed on the surface of the $SnO_2$ thin film:

When the gas absorbed on the surface of the $SnO_2$ thin film is acceptor oxygen, for example $O_2^{-1}$, $O^{-1}$, and $O^{-2}$, a depletion region is formed on the surface of the $SnO_2$ thin film to reduce conduction electrons and increase the resistance. At this moment, the test gas, for example CO, will react with the acceptor oxygen to form $CO_2^{-1}$. Some electrons are excited to return to the conduction band to increase conduction electrons and reduce the resistance.

An ethanol gas sensor with a "$SnO_2$ thin film/Ag electrode/$Al_2O_3$ substrate" structure is stated as follows.

Figure 1A:
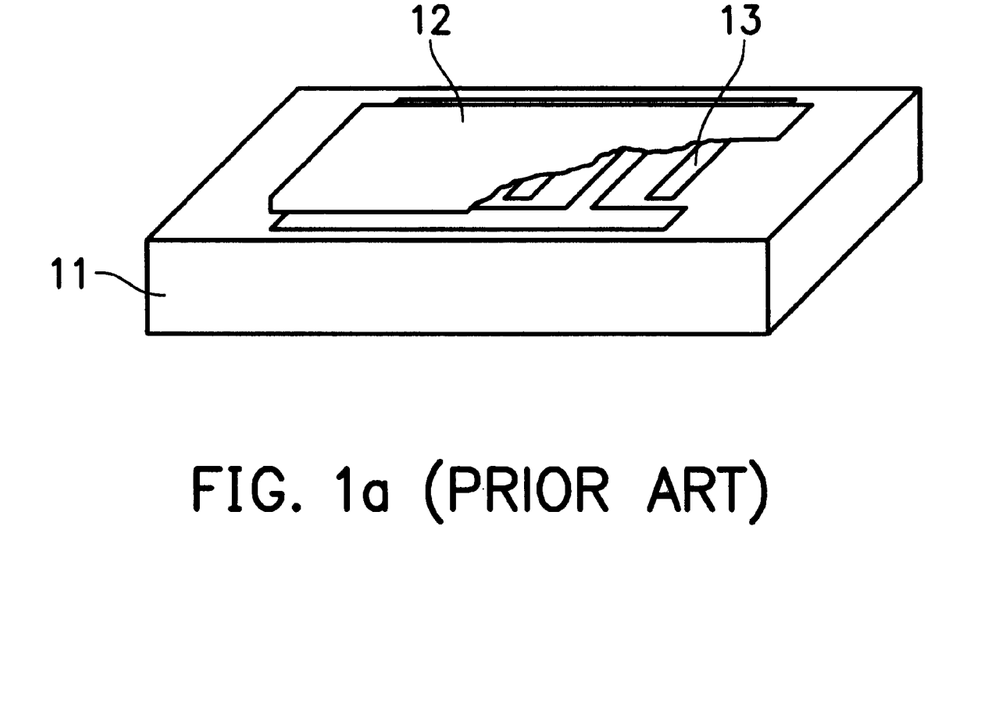
FIG. 1a is a structural diagram of the gas sensor with a "$SnO_2$ thin film/Ag electrode/$Al_2O_3$ substrate" structure.
Figure 1B:
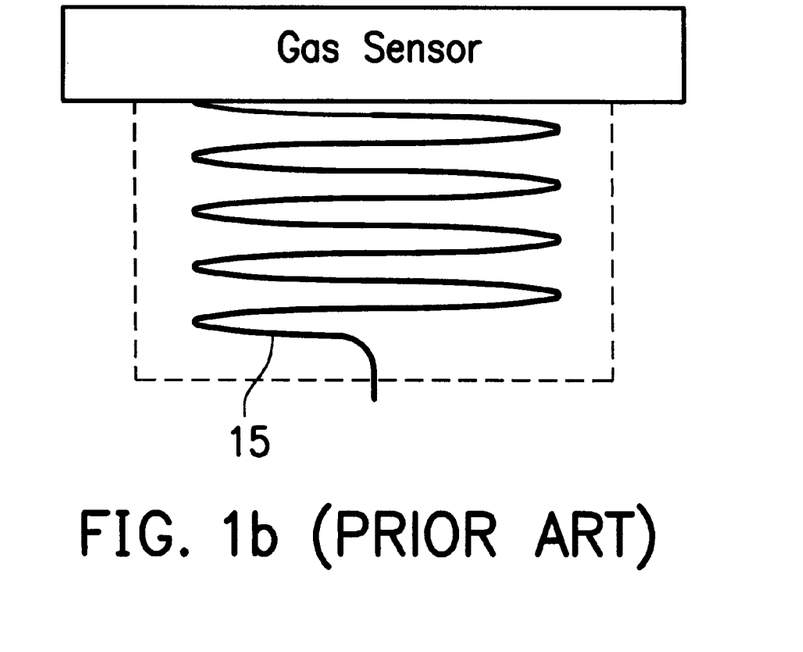
FIG. 1b is a diagram showing the gas sensor shown in FIG. 1a with a Pt-coil heater.

FIG. 1a depicts a structural diagram of a ethanol gas sensor with a "$SnO_2$ thin film/Ag electrode/$Al_2O_3$ substrate" structure, wherein reference numbers 11, 12, and 13 represent the $Al_2O_3$ substrate, $SnO_2$ thin film, and Ag electrode, respectively. FIG. 1b depicts a diagram showing a gas sensor with a Pt-coil heater 15. To improve the characteristics of the gas sensor, the operating temperature normally ranges from 300° C. to 400° C. Therefore, a heater is needed for heating the gas sensor to this operating temperature.

When the test gas comes in, a part of the test gas reacts with the surface of the $SnO_2$ thin film 12 for forming a Schottky contact to enlarge the resistance the $SnO_2$ thin film 12. This reaction belongs to mode (1). Another part of the test gas reacts with the acceptor oxygen, which is absorbed on the surface of the $SnO_2$ thin film 12, to reduce the resistance of the $SnO_2$ thin film 12. This reaction belongs to mode (2). The test gas is identified by a change of the resistance of the $SnO_2$ thin film 12.

When the operating temperature is 300° C., the sensitivity, reaction time, and recovery time of the ethanol gas with a concentration of 1500 ppm are 130, 10 seconds, and 30 seconds, respectively. In contrast, the sensitivity, reaction time, and recovery time of the $H_2$ gas with a concentration of 1500 ppm are 12, 3 minutes, and 1 minute, respectively.

However, the heater of the gas sensor is not completely thermal-insulated from the outside. Thermal dissipation easily occurs at the main sensing part potentially reducing the sensitivity of the gas sensor. Further, if the material of the heater does not have good thermal stability, the heater is easily affected by the external temperature and humidity thereby making the gas sensor of the prior art unsuitable for testing gas with a high concentration. And, because the main sensing part can not be made into an array structure, the gas sensor does not perform well in a large scanning area. The total physical size of the gas sensor is not easily reduced. Therefore, the power consumption is high, and the system speed is low.

SUMMARY OF THE INVENTION

Therefore, a high performance ethanol gas sensor is needed to overcome the disadvantages of the prior art and provide an improved structure.

In order to achieve the above objects, the present invention provides a high performance ethanol gas sensor and fabrication method thereof, which applies an MEMS technology and a VLSI process to make it suitable for wide area testing and to meet the requirements of low power consumption, high speed, small physical size. In addition, when attached to microcomputer system, the present invention can identify the component and concentration of the test gas. In the present invention, the structure of the main sensing elements are of cantilever-bridge structure, and the SiC heater and the $SiO_2$ thin film are integrated on the same silicon chip.

DESCRIPTION OF THE DRAWINGS

Other objects, features, and advantages of the present invention will become apparent from the following detailed description made with reference to an illustrative but non-limiting embodiment. The description is made with reference to the accompanying drawings, in which:

FIGS. 10a and 10b are diagrams depicting comparisons between the prior art, the single cantilever-bridge structure, and the double cantilever-bridge structure of the present invention, wherein

DESCRIPTION OF THE PREFERRED EMBODIMENT

Figure 2A:
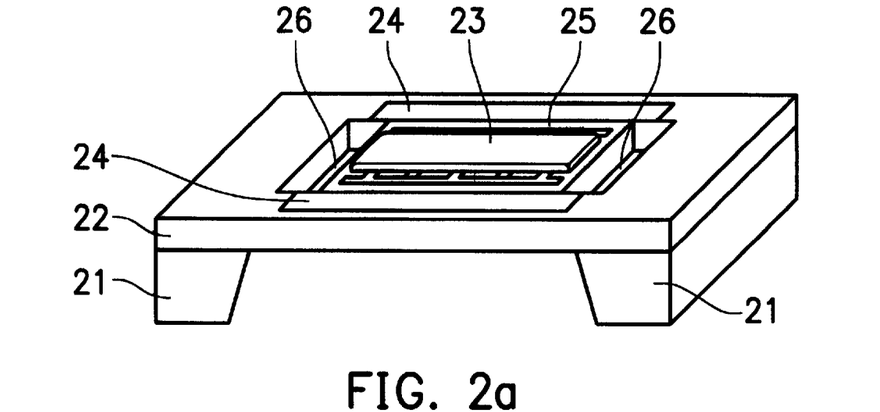
FIGS. 2a~2c are a perspective view, a front cross-sectional view, and a top view, respectively of the gas sensor of the present invention.
Figure 2B:
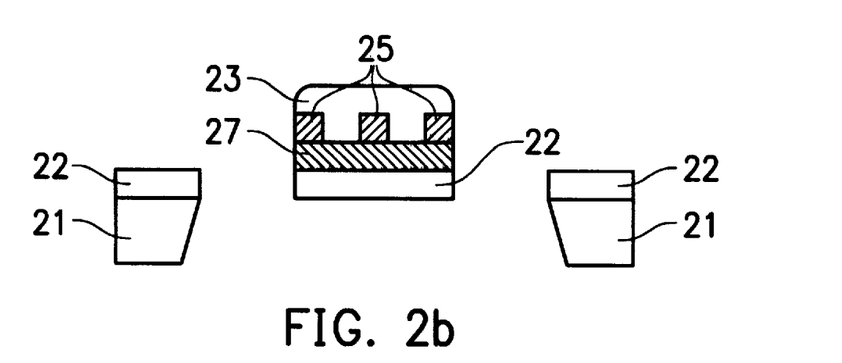
Figure 2C:
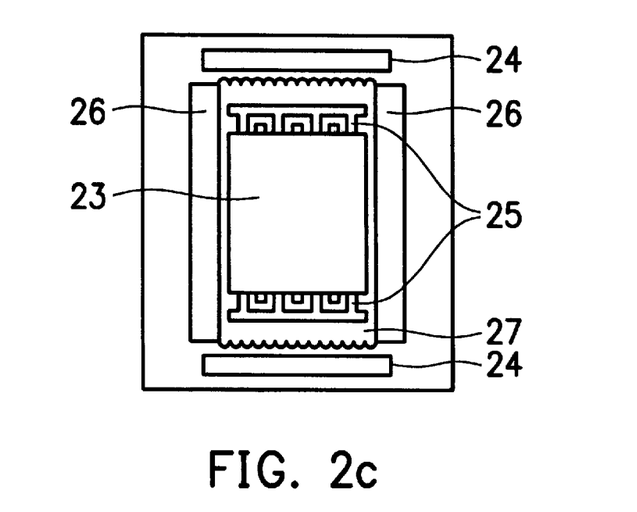

FIGS. 2a~2c are a perspective view, a front cross-sectional view, and a top view of the gas sensor of the present invention, respectively. In FIG. 2a~2c, reference numbers 21, 22, 23, 24, 25, 26, and 27 represent Si substrate, SiC thin film and SiC heater, $SiO_2$ thin film, Al electrode, finger Ag electrode, hollow region, and $Al_2O_3$ thin film, respectively. The shape of the heater 22 in FIG. 2b shows a single cantilever-bridge structure.

Figure 3:
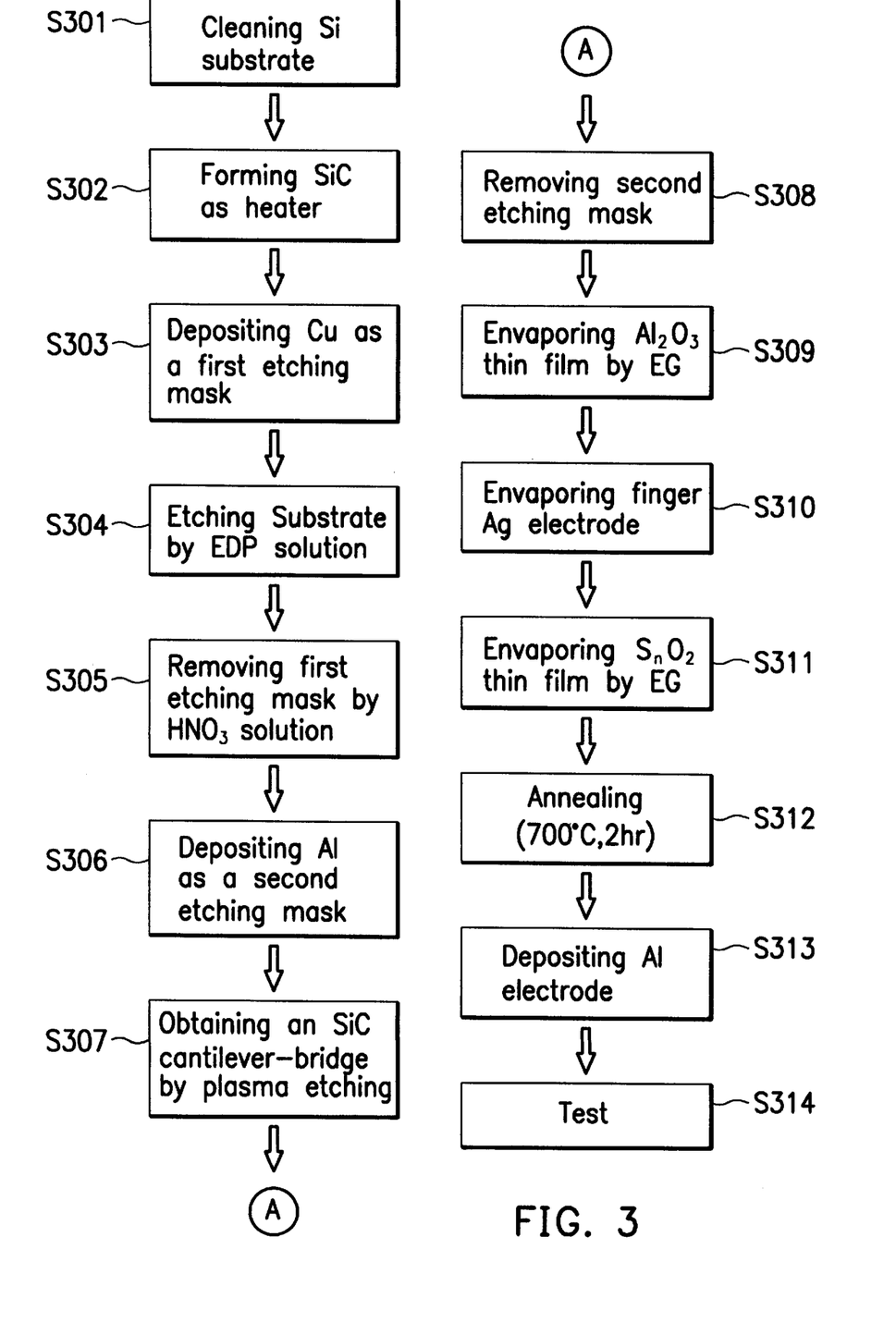
FIG. 3 is a fabrication flow chart of the preferred embodiment of the present invention.

FIG. 3 and FIGS. 4a~4k shows the fabrication process of the ethanol gas sensor of the-present invention. FIG. 3 is a fabrication flow chart of the embodiment of the present invention. FIGS. 4a~4k are diagrams corresponding to some fabrication steps shown in FIG. 31.

Figure 4A:
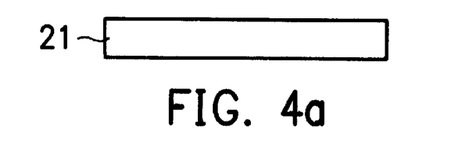
FIGS. 4a~4k are diagrams corresponding to some fabrication steps shown in FIG. 3.
Figure 4B:
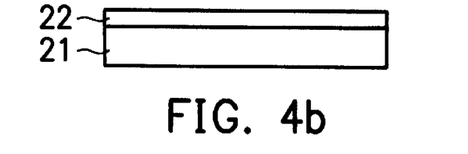

First, the Si substrate 21 is cleaned, as stated in step S301. The Si substrate 21 of this embodiment has a resistance of 1~10 ohm-cm, and a thickness of 406~457 $\mu$m. The result from step S301 is shown in FIG. 4a. Then, as stated in step S302, the cleaned Si substrate 21 is placed in a RTCVD (rapid thermal chemical vapor deposition) system to deposit a SiC thin film 22 as a heater material. The SiC thin film 22 has a forming temperature of 1150° C., and a thickness of 550~1000 Å. The result from step S302 is shown in FIG. 4b.

Figure 4C:
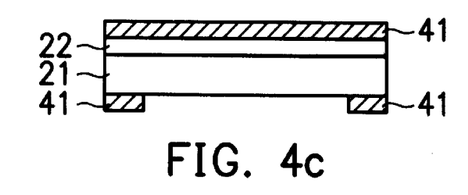
Figure 4D:
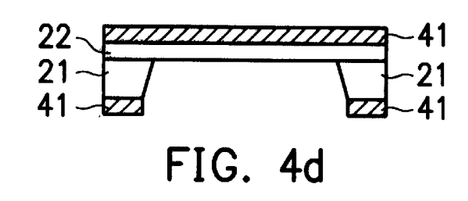

In step S303, a Cu thin film is formed as a first etching mask 41. The first etching mask is formed at a predetermined place under the Si substrate 21 and above the SiC thin film 22. FIG. 4c clearly shows the predetermined place. Then, as stated in step S304, the Si substrate 21 is wet-etched by EDP solution. The EDP solution used here is obtained by dissolving 120 ml of EthyeleneDiamine and 20 gw of Pyrocatechol in 60 ml of deionized water. In the wet etching, the etching temperature is 100° C., and the etching speed is 72 $\mu$m/hr. FIG. 4d depicts the shape after wet etching.

Figure 4E:
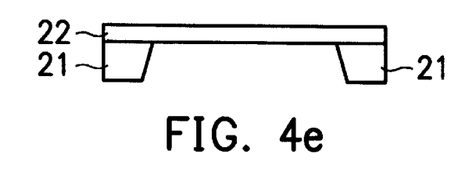
Figure 4F:
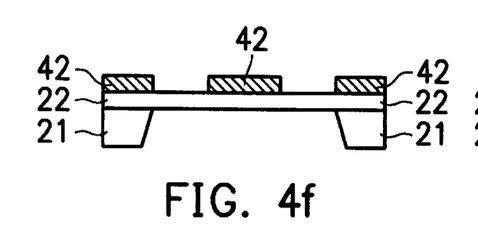

Then, as stated in step S305, the first etching mask 41 is removed by $HNO_3$ solution ($HNO_3$: $H_2O$=1: 5), as shown in FIG. 4e. Then, as stated in step S306, an Al thin film is formed on the SiC thin film 22 as a second etching mask 42, as shown in FIG. 4f. The second etching mask 42 is used to define a cantilever-bridge area of the SiC thin film 22 with an effective area of 0.5×1.5 mm² and a thickness of 4.5 $\mu$m.

Figure 4G:
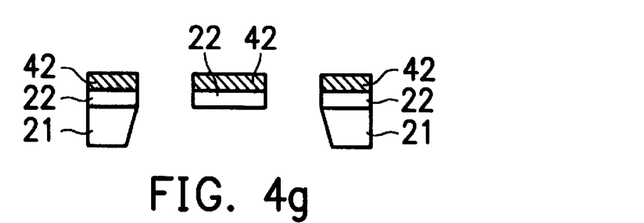
Figure 4H:
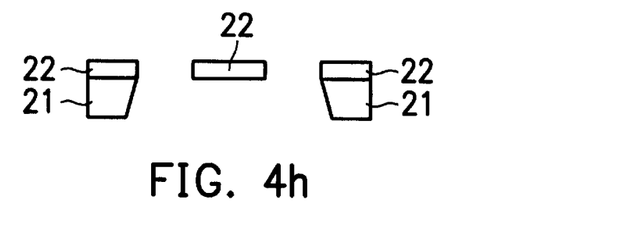

Then, as stated in step S307, the second etching mask 42 is etched via a plasma etching process. The result obtained is shown in FIG. 4g. The residual second etching mask 42 is etched by a heated solution ($H_3PO_4$:$HNO_3$:$CH_3COOH$:$H_2O$=50:3:3:3), as stated in step S308. The result obtained from step S308 is shown in FIG. 4h.

Figure 4I:
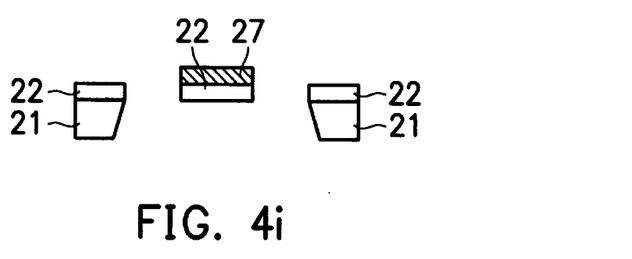
Figure 4J:
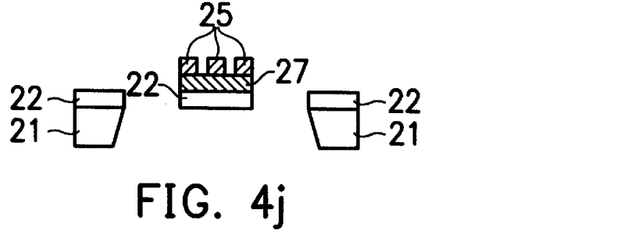

Then, as stated in step S309, an $Al_2O_3$ thin film 27 with a thickness of 1000 Å is formed on the SiC thin film 22 via an EG (electron-gun) system with a pressure of $10^{-5}$ torr. The result after step S309 is shown in FIG. 4i. Then, a finger Ag electrode 25 is formed at a predetermined place on the $Al_2O_3$ thin film 27, as stated in step S310. The Ag electrode 25 has a thickness of 2000~4000 Å, and a shape as shown in FIG. 4j. At this moment, total structure is placed in an $N_2$ furnace for an hour of heat processing.

Figure 4K:
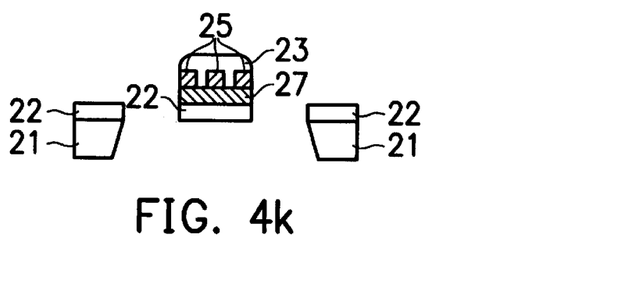

Then, as stated in step S311, an $SnO_2$ thin film 23 with a thickness of 600 Å is formed at a predetermined place on the cantilever-bridge and the Ag electrode 25. The shape of the $SnO_2$ thin film 23 is shown in FIG. 4k. In step S312, the total structure is placed in an annealing furnace of 700° C. for two hours of annealing process.

Then, in step S313, at two ends of the cantilever-bridge, the electrode region of the; heater is defined for forming an Al thin film as an Al electrode 24. Finally, in step S314, the gas sensor is put in a air-simulation cavity for an ethanol gas test. In the air-simulation cavity, the ratio of $O_2$:$N_2$ is 1:4, and the atmosphere pressure is 1 torr.

Figure 5:
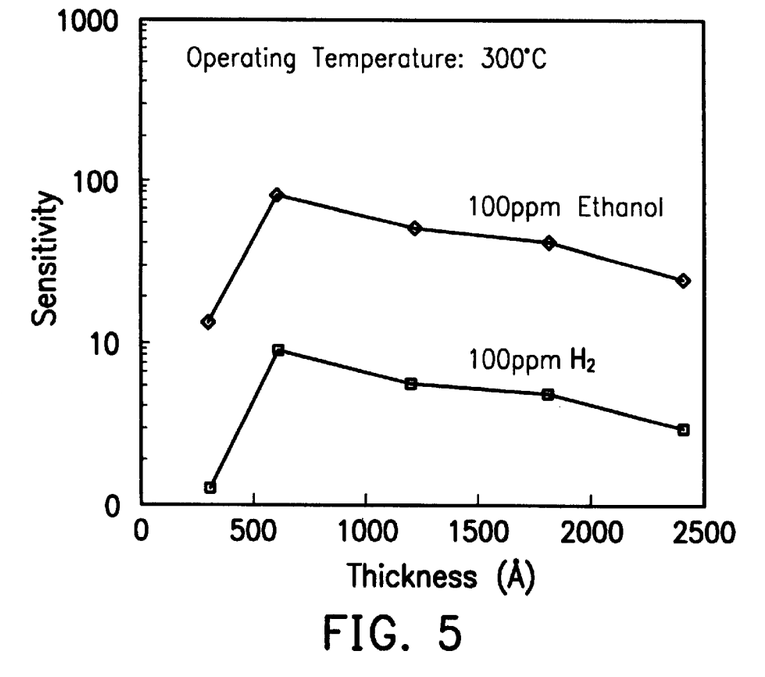
FIG. 5 is a diagram depicting the relationship between the sensitivity and the thickness of the $SnO_2$ thin film of the present invention.

The following explains why the $SnO_2$ thin film has a thickness of 600 Å. FIG. 5 depicts the relationship between the sensitivity and the thickness of the $SnO_2$ thin film of the embodiment at the operating temperature of 300° C. and a concentration of 1000 ppm. From FIG. 5, it is known the sensitivity is highest when the $SnO_2$ thin film has a thickness of 600 Å; and lowest when the $SiO_2$ thin film has a thickness of 300 Å. That is because the $SnO_2$ thin film with a thickness of 300 Å is not complete in structure. However, when the thickness is greater than 600 Å, the sensitivity is reduced. The sensitivity is in proportional to an average contact area between the thin film and the test gas. However the total contact area between the thin film and the test gas is fixed in some cases. If the thickness of the thin film is larger, the physical size of the thin film is larger, resulting in a smaller average contact area, and reduced sensitivity.

Figure 6:
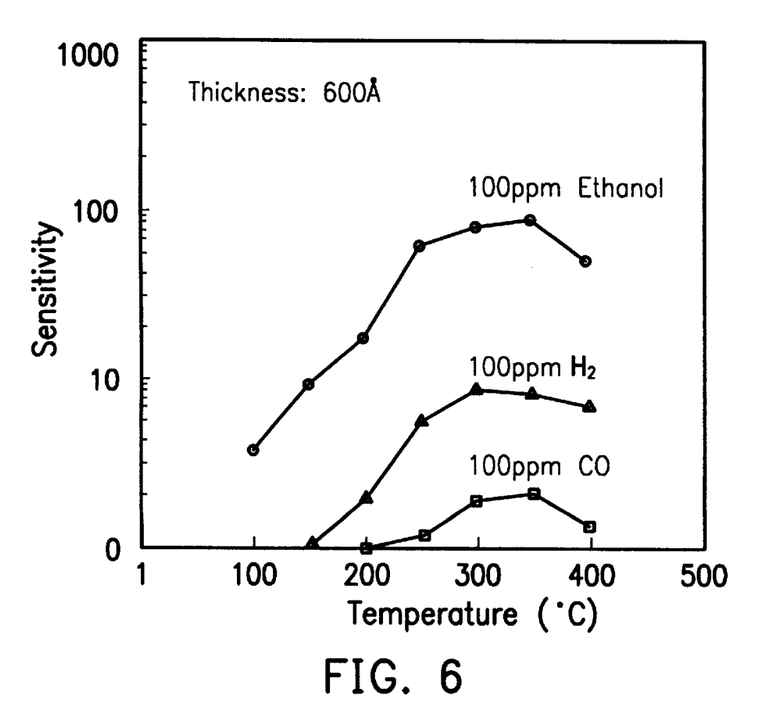
FIG. 6 is a diagram depicting the relationship between the sensitivity and the operating temperature.

The following explains the relation between the operating temperature and the sensitivity when the $SnO_2$ thin film has a fixed thickness of 600 Å. FIG. 6 depicts the relationship between the operating temperature and the sensitivity. From FIG. 6, the highest sensitivity of ethanol gas and CO gas with a concentration of 1000 ppm are 80~90 and 1~2 at an operating temperature of 300~350° C., respectively. The highest sensitivity of $H_2$ gas is about 8.9 at an operating temperature of 300° C. From FIG. 6, it is clear that the sensitivity is low when the operating temperature is under 300° C. Above 300° C., the higher the operating temperature, the higher the sensitivity. However, the sensitivity drops when the operating temperature exceeds 350° C. This is because when the operating temperature is too low, it is difficult for the chemical reaction to overcome the activation energy Ea, so the sensitivity is low. As the operating temperature is higher, it is easier for the chemical reaction to overcome the activation energy Ea; and the sensitivity is increased. When the operating temperature reaches a certain degree, the sensitivity reaches its preferred value. If the operating temperature continues to increase, it becomes difficult for the test gas to be absorbed.

Figure 7:
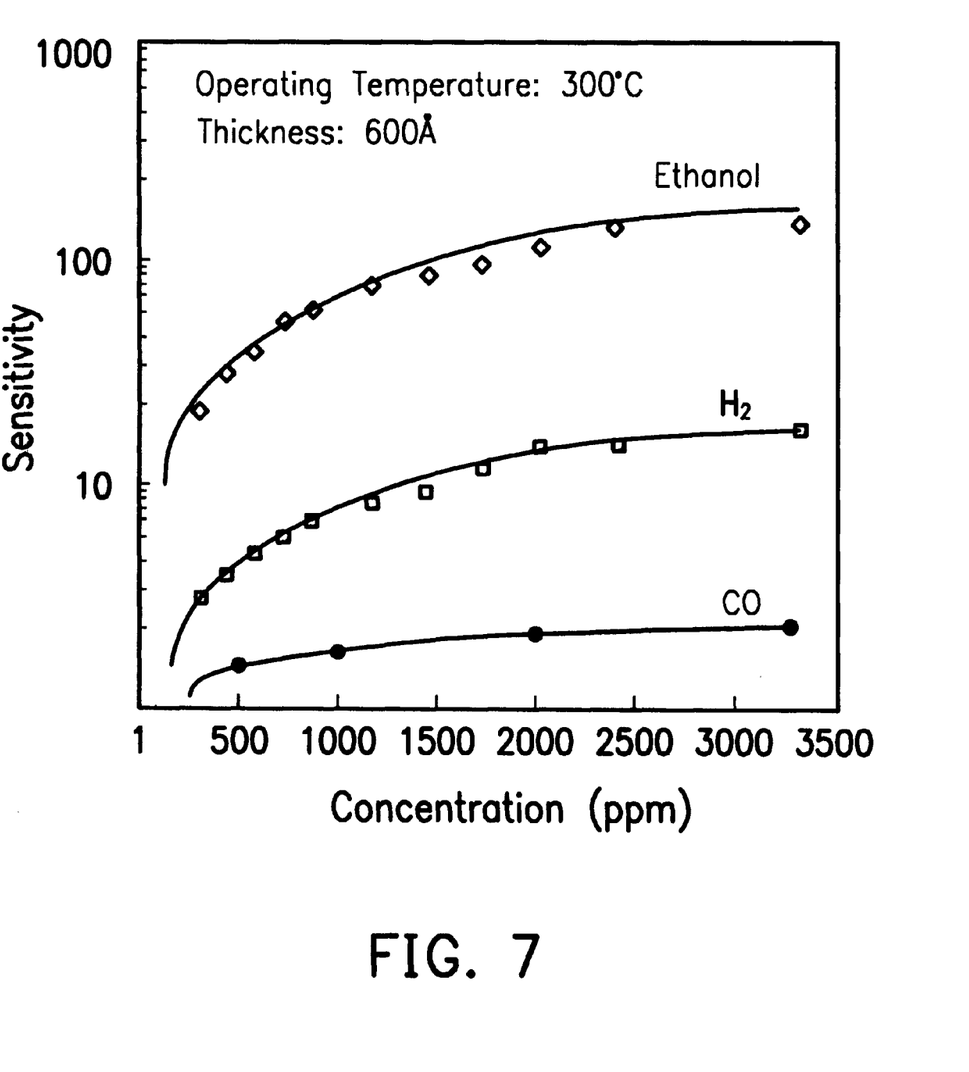
FIG. 7 is a diagram depicting the relation between the sensitivity and the concentration of the test gas.

The following explains the sensitivity of different test gases when the operating temperature is 300° C. and the $SnO_2$ thin film has a thickness of 600 Å. FIG. 7 depicts a comparison from ethanol gas, $H_2$ gas and CO gas. From FIG. 7, it is evident that the ethanol gas has a higher sensitivity than the $H_2$ gas, which has a higher sensitivity than the CO gas. The present invention provides a good selectivity because a large difference in sensitivity exists between different test gases. The higher the concentration of the test gas, the higher the corresponding sensitivity. This is because when the concentration is higher, more gas molecules are absorbed on the surface of the SnO$_2$ thin film. Therefore, the sensitivity is increased.

Figure 8:
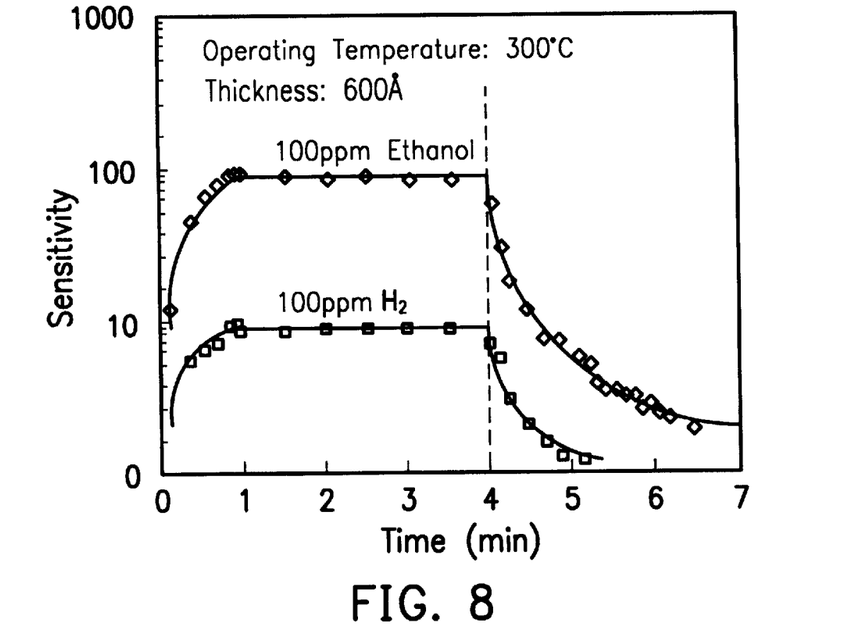
FIG. 8 is a diagram depicting the reaction time and the recovery time of the single cantilever-bridge element of the present invention.

FIG. 8 is a diagram depicting the reaction time and the recovery time of the present invention. From FIG. 8, it is evident that the ethanol gas with a concentration of 1000 ppm has a reaction time of 20 seconds and a recovery time of 2~3 minutes. The H$_2$ gas with a concentration of 1000 ppm has a reaction time of 30~40 seconds and a recovery time of 40 seconds~1 minute.

Figure 9:
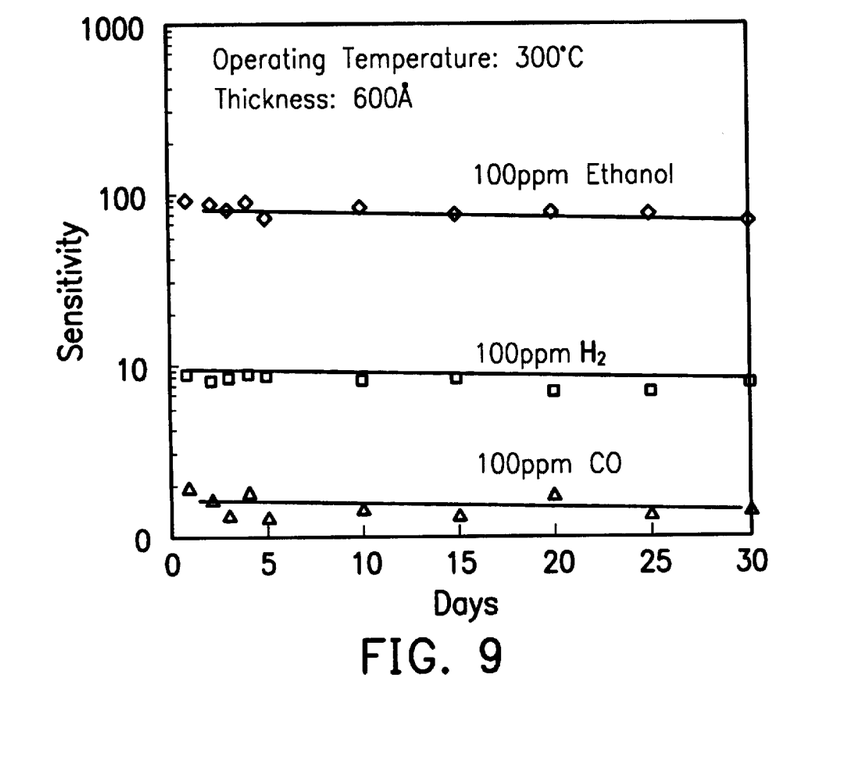
FIG. 9 is a diagram showing the stability of the present invention over a long period of time.

FIG. 9 is a diagram depicting the sensitivity of ethanol gas, H$_2$, gas, and CO gas with concentrations of 1000 ppm in a test period of one month when the operating temperature is 300° C. and the SnO$_2$ thin film has a thickness of 600 Å. FIG. 9 indicates that the sensitivity in the one-month test period does not change much, so the present invention has good stability.

Figure 11:
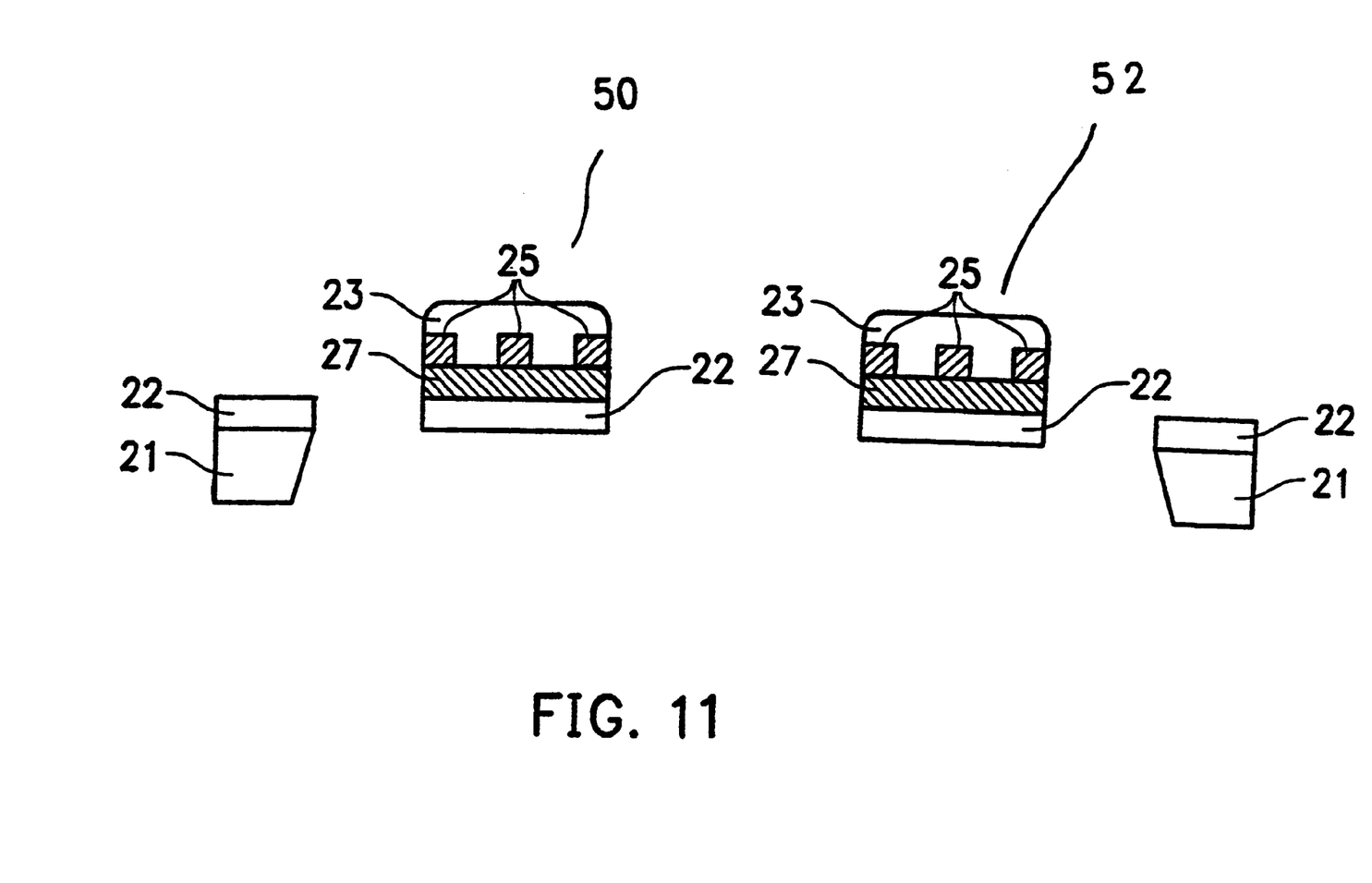
FIG. 11 is a front cross-sectional view of a gas sensor according to another embodiment of the present invention which employs the double cantilever-bridge structure.

FIG. 11 provides a front cross-sectional view of the gas sensor according to another embodiment of the present invention which employs a double cantilever-bridge structure. As shown, the double cantilever-bridge structure includes a first bridge structure 50 and a second bridge structure 52 each formed and structured in a manner similar to the single cantilever-bridge structure illustrated in FIGS. 2–4.

Figure 10A:
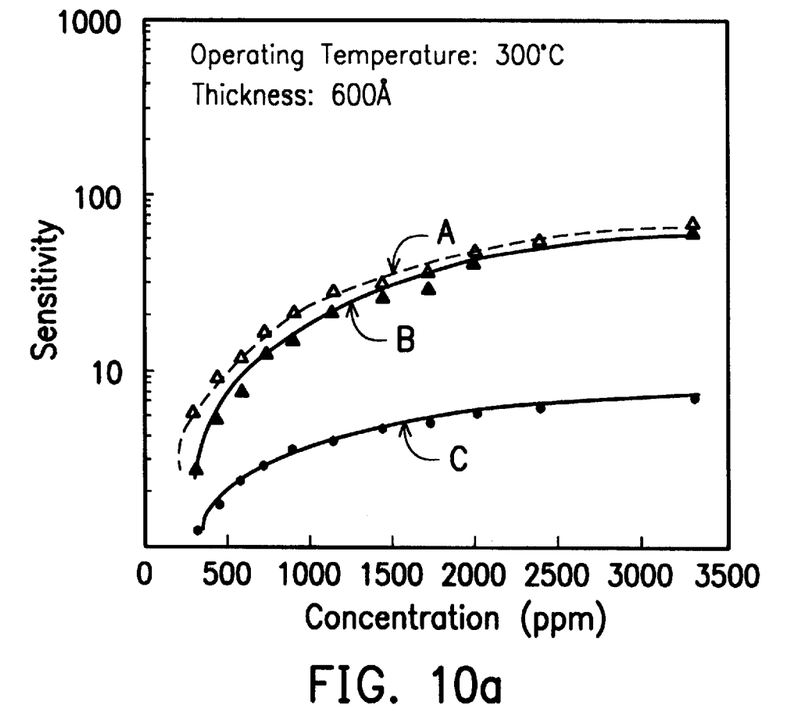
FIG. 10a is a diagram showing the sensitivity under different concentrations of ethanol gas.
Figure 10B:
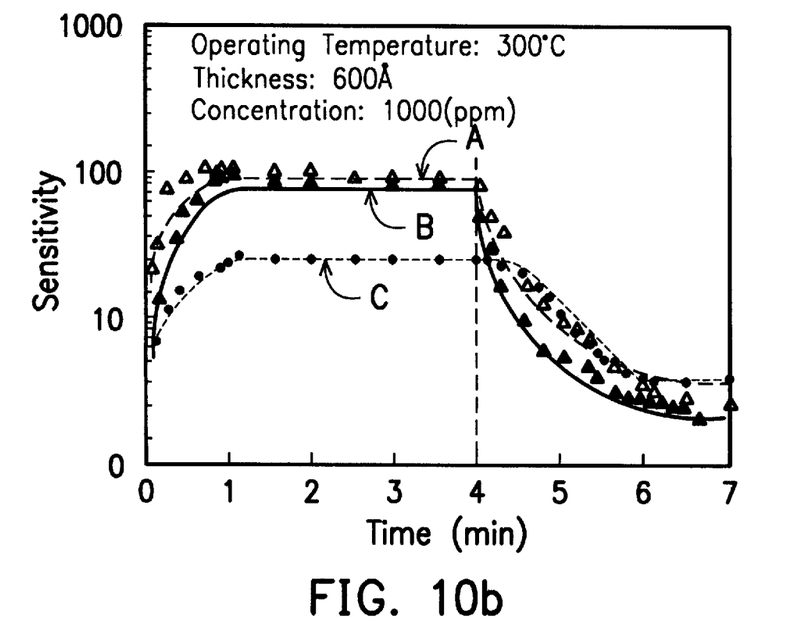
FIG. 10b is a diagram showing the reaction time and the recovery time of the present invention.

FIG. 10a and 10b are diagrams depicting comparisons between the prior art, and, the single cantilever-bridge structure and the double cantilever-bridge structure of the present invention, wherein FIG. 10a is a diagram showing the sensitivity under different concentrations of ethanol gas, and FIG. 10b is a diagram showing the reaction time and the recovery time of the present invention.

FIG. 10a shows that the double cantilever-bridge structure has a higher sensitivity by 10~20 than the single cantilever-bridge structure when the operating temperature is 300° C. and the SnO$_2$ thin film has a thickness of 600 Å. That is because the former has a larger surface area than the latter. As described above, the sensitivity is in proportion with the surface area. The sensitivity of structures is almost twice that of the prior art.

Referring to FIG. 10b, compared with the single cantilever-bridge structure, the double cantilever-bridge structure has a shorter reaction time of 10~20 seconds, and a longer recovery time of about 3 minutes. The reaction time and the recovery time of them both are shorter than the prior art.

Some physical parameters of SiC material, Si material, and GaAs material are shown in following TABLE 1.

TABLE 1

|  | SiC | Si | GaAs |
|---|---|---|---|
| Energy gap (300° K.) (eV) | 2.2 | 1.12 | 1.43 |
| Thermal Conductivity (w/cm-° C.) | 5.0 | 1.5 | 0.5 |
| Young's Modulus (GPa) | 448 | 190 | 75 |
| Breakdown Voltage (10$^6$V/cm) | 4 | 0.3 | 0.4 |
| Melting Point (° C.) | 2830 | 1415 | 1238 |

Referring to TABLE 1, compared with Si material and GaAs material, SiC material is characterized by a wide energy gap, good thermal conductivity, a high Young's modulus, a larger breakdown voltage, and a high melting point. That is why the heater of the present invention is made of SiC material.

In conclusion, the present invention is characterized by:

(1) a heater made of SiC material, for obtaining a faster rate of temperature rise because of its good thermal stability and thermal conductivity;

(2) a main sensing part of cantilever-bridge, for the heater to raise heating efficiency and the sensitivity and the reaction rate thereof;

(3) compatiblility with current VLSI technology to develop Application Specific IC (ASIC), or duplication into an array structure to raise sensitivity; and (4) fabrication of a few cantilever-bridge structures into an array structure for high performance.

Although the invention in connection with preferred embodiments has been described, modifications will now doubtlessly be apparent to those skilled in this technology. The foregoing description of the preferred embodiments of the invention has been provided for the purposes of illustration and description. It is not intended to be exhaustive or to limit the invention to the precise embodiment disclosed herein. The disclosed embodiment has been chosen and described to best explain the principles of the invention and its practical application, thereby enables others skilled in this technology to understand the invention, to practice various other embodiments thereof and to make various modifications suited to the particular use contemplated of the present invention. As such, it is intended that the scope of this invention shall not be limited to the disclosed embodiments presented here, but rather shall be defined by the following claims and their equivalents.

What is claimed is:

1. An integrated ethanol gas sensor, comprising:

a Si substrate;

an SiC thin film formed on a predetermined location of said Si substrate, said SiC thin film including a cantilever-bridge structure;

a first thin film, formed on said SiC thin film;

a finger electrode, formed on said first thin film; and a second thin film, formed on a predetermined location of said finger electrode, said second thin film defining a gas sensing element and being disposed substantially completely upon said cantilever-bridge structure without any substantial covering of said gas sensor and first thin film away from the cantilever-bridge structure.

2. The integrated ethanol gas sensor of claim 1, wherein said Si substrate has a thickness of 406~457 μm and a resistance of 1~10 ohm—cm.

3. The integrated ethanol gas sensor of claim 1, wherein said SiC thin film has a thickness of 550~1000 Å and a formation temperature of 1150° C.

4. The integrated ethanol gas sensor of claim 1, wherein said first thin film is an Al$_2$O$_3$ thin film with a thickness of 1000 Å.

5. The integrated ethanol gas sensor of claim 1, wherein said finger electrode is an Ag finger electrode with a thickness of 2000~4000 Å.

6. The integrated ethanol gas sensor of claim 1, wherein said second thin film is an SnO$_2$ thin film with a thickness of 600 Å.

7. The integrated ethanol gas sensor of claim 1, wherein said cantilever-bridge structure of said SiC thin film comprising a single cantilever-bridge structure.

8. The integrated ethanol gas sensor of claim 1, wherein said cantilever-bridge structure of said SiC thin film comprising a double cantilever-bridge structure.

* * * * *